United States Patent
Wei (10) Patent No.: US 7,273,050 B2
(45) Date of Patent: Sep. 25, 2007

(54) JET ENDOTRACHEAL DEVICE AND ITS USE IN INTUBATION

(76) Inventor: Huafeng Wei, 20 Forest Hill Dr., Cherry Hill, NJ (US) 08003

( * ) Notice: Subject to any disclaimer, the term of this patent is extended or adjusted under 35 U.S.C. 154(b) by 190 days.

(21) Appl. No.: 10/908,194

(22) Filed: May 2, 2005

(65) Prior Publication Data

US 2005/0279360 A1    Dec. 22, 2005

Related U.S. Application Data (60) Provisional application No. 60/567,682, filed on May 3, 2004.

(51) Int. Cl.
*A61M 16/00* (2006.01)
*A62B 7/00* (2006.01)
(52) U.S. Cl. ............ 128/200.26; 128/204.18; 128/207.14
(58) Field of Classification Search ........ 128/200.26, 128/204.18, 204.25, 204.26, 205.12, 205.23, 128/207.14, 207.15, 207.16, 204.23
See application file for complete search history.

(56) References Cited

U.S. PATENT DOCUMENTS

| | | | |
|---|---|---|---|
| 4,270,530 A * | 6/1981 | Baum et al. ............ 128/204.25 |
| 4,387,784 A | 6/1983 | Hill | |
| 4,488,548 A | 12/1984 | Agdanowski | |
| 4,584,998 A | 4/1986 | McGrail | |
| 4,777,961 A | 10/1988 | Saltzman | |
| 5,031,613 A * | 7/1991 | Smith et al. ............ 128/207.14 |
| 5,235,970 A * | 8/1993 | Augustine ............ 128/200.26 |
| 5,285,778 A * | 2/1994 | Mackin ................. 128/207.15 |
| 5,372,131 A * | 12/1994 | Heinen, Jr. ............ 128/207.15 |
| 5,445,161 A | 8/1995 | Huang | |
| 5,636,625 A * | 6/1997 | Miyagi et al. ......... 128/200.26 |
| 5,642,730 A * | 7/1997 | Baran .................... 128/207.14 |
| 5,964,223 A * | 10/1999 | Baran .................... 128/207.14 |
| 6,098,617 A * | 8/2000 | Connell ................. 128/200.26 |
| 6,102,042 A * | 8/2000 | Hete et al. ............. 128/207.16 |
| 6,164,277 A | 12/2000 | Merideth | |
| 6,568,388 B2 | 5/2003 | Christopher | |
| 2004/0000314 A1 | 1/2004 | Angel | |

FOREIGN PATENT DOCUMENTS

WO    WO91/12044    * 8/1991

* cited by examiner

*Primary Examiner*—Teena Mitchell
(74) *Attorney, Agent, or Firm*—Evelyn H. McConathy; Montgomery, McCracken, Walker, & Rhoads, LLP (57) ABSTRACT

An endotracheal device includes a unit with a pair of tubes and a beveled distal end. One tube is used for jet ventilation, while a monitoring catheter is provided inside the second, larger tube. The device is useful for otherwise difficult intubations.

20 Claims, 4 Drawing Sheets

JET ENDOTRACHEAL DEVICE AND ITS USE IN INTUBATION

CROSS-REFERENCE TO RELATED APPLICATION

This application claims the benefit of U.S. Provisional Patent Application No. 60/567,682 filed May 3, 2004.

BACKGROUND OF THE INVENTION

1. Field of the Invention

The present invention relates to endotracheal devices and the use of such devices in the intubation of a patient.

2. Brief Description of the Prior Art

During surgery and other medical procedures it is often necessary to insert an endotracheal tube ("ET") into the trachea of a patient for the purposes of ventilation assistance, or otherwise. It is sometimes necessary, such as in emergency situations of cardiac arrest, acute respiratory failure or airway obstruction etc, to position an ET rapidly. Failure to properly position an ET, or failure to insert an ET quickly, can result in severe medical complication or even death.

For example, in an emergency cesarean section occasioned by fetus distress or other reasons, emergency placement of an ET in a mother's trachea is often required for general anesthesia. Failure to perform a rapid intubation after induction of general anesthesia may lead to severe damage.

There are numerous ways to intubate a trachea, the choice of which depends on the preference of the medical personnel and the anatomy of the patient's airway. For a patient of an expected normal airway, most anesthesiologists chose to intubate a patient after induction of unconsciousness and use of muscle relaxants. The glottis of a patient can be viewed under the direct laryngoscopy. Four grades of view of the glottis have been classified (Cormack, R. S. and Lehane J., "Difficult tracheal intubation in obstetrics," *Anesthesia* 1984; 39: 1005-1111): Grade I, full view of the glottis; Grade II, posterior portion of the glottis is visible; Grade III, only tip of the epiglottis is visible; Grade IV, only soft palate is visible.

It is usually easy and possible to intubate a trachea with Grade I or II view, but it is often difficult or impossible to intubate trachea with Grade III or IV view rapidly when employing only direct laryngoscopy to assist in the intubation. It is not uncommon that an expected normal airway may turn out to be a Grade III or IV view of the glottis after paralyzing a patient and inspecting the airway using direct laryngoscopy. Furthermore, it is sometimes not possible to either ventilate a patient with a facial mask and or to intubate the patient (so called "non-intubation and non-ventilation airway emergency"). Therefore, in such situation it may prove lifesaving that proper oxygenation is maintained before intubation, and that intubation is accomplished as quickly as possible.

Compared to conventional mechanical ventilation ("CVM"), high frequency jet ventilation (HFJV) is characterized by its opening system, low tidal volume and low airway pressure. It is almost impossible to perform CMV before tracheal intubation in the situation described above, because it requires a close breathing circuit for positive pressure ventilation. However, it is possible to perform jet ventilation using a jet catheter before tracheal intubation, thus maintaining effective oxygenation and/or ventilation during intubation, which in turn, can prolong the time allotted for intubation in patients with Grade view III or IV and increase the safety of intubation.

In the case of an airway for which intubation is expected to be difficult, a fiber-optic guide device is frequently employed. However, such fiber-optic devices are usually used when the patient is awake, and not under general anesthesia. As currently practiced, fiber-optic assisted intubation does not provide sufficient oxygenation and/or ventilation before intubation. On the other hand, it is often difficult to intubate quickly enough a patient who is not breathing spontaneously using fiber-optic guided intubation to avoid worsening the patent's oxygenation, even at the hands of experienced medical personnel. Other shortcomings of fiber-optic assisted intubation include the fact that the glass fibers have a tendency to break after use, and the fiber optic lens can become dislocated and are expensive to replace. In addition, quite often secretions and blood in the airway can totally obscure the visual field. Therefore, in the situation of an unexpectedly difficult airway, it is impractical to do an emergency fiber-optic guided intubation.

Laryngeal mask airway ("LMA") is used as a back-up airway management technique for unexpectedly difficult airways in most situations. However, LMA can not be used for long-term positive pressure ventilation or to protect the airway from aspiration. These drawbacks will limit its use in many emergency situations, such as during cardiopulmonary resuscitation, in a patient with a full stomach, and in acute respiratory failure, etc. Ultimately, LMA has to be changed to a trachea intubation with an ET for effective positive pressure ventilation.

Transtracheal jet ventilation has been recommended by the American Society of Anesthesiologist (ASA) in emergency situations of "cannot intubate, cannot ventilate" as a rescue method. This requires a percutaneous puncture of large bore (>G14) catheter into trachea and is quite invasive to patient. Often, anesthesiologists are not well trained to use transtracheal jet ventilation because of lack of practice in non-emergency situations where the method is infrequently employed because of its invasiveness and possible complications. Meanwhile, the lack of expiratory pathway for the jet pulse in the obstructed upper airway may increase the likelihood of barotraumas.

An audio-guided intubation stylet has been designed to guide tracheal intubation (U.S. Pat. No. 6,164,277). However, spontaneous breathing must be maintained to guide the ET. In the most situations, medical personnel prefer to intubate a patient after induction of general anesthesia and muscle relaxation. Under these circumstances, patients do not experience the discomfort otherwise associated with intubation, and less time is required to accomplish the intubation than when the patient is awake.

Another endotracheal assembly (U.S. Pat. No. 4,488,548) has been designed to prevent the whip effect of an insufflation catheter inside endotracheal tube and/or trachea, and to maximize air entrance during jet ventilation. In this case, the ET has spacers adjacent the distal end to space the insufflation catheter from the inner side walls of the tube. However, the insufflation catheter is not designed as a guide for intubation, and the distal end of insufflation catheter is well positioned as a guide into trachea.

An endotracheal assembly has been designed with the jet nozzles inside the ET (U.S. Pat. No. 4,270,530) to reduce turbulent during HFJV at a frequency above 600/min. Two jet nozzles spaced from each other inside ET are connected to separate feed lines. Although this arrangement permits selective ventilation of the lungs by gas currents adapted to the existing resistance conditions, it is not suitable to be utilized as a guiding catheter for intubation.

Christopher (U.S. Pat. No. 6,568,388) discloses a method and apparatus for guiding insertion of an endotracheal tube into a patient's trachea while continuing to supply air/oxygen in the patient's airway and lungs. The shortcoming of this design is that the intubation guide has a fixed angle on the distal end, thus it is unable to be adapted to the different view of glottis efficiently and quickly (e.g. a throat of Grade III may be higher than in Grade II). This makes it difficult to view the glottis with the fiber-optic device quickly in emergency situation. In addition, it will be difficult for the distal end of oxygen supplying catheter directly facing the vocal cord opening to provide adequate oxygenation and ventilation, while at the same time to adjust the distal end of the fiber-optic device for a good view of the glottis.

Huang (U.S. Pat. No. 5,445,161) discloses an apparatus and method for accurately securing an airway for the purpose of endotracheal intubation of a patient using a computed capnogram. The major shortcoming of this design is that the patient must have spontaneous breathing in order to use the capnogram as a guiding device. Patients are usually paralyzed with muscle relaxant to achieve maximum exposure of the glottis for intubation, and thus such patients are likely to develop apnea, especially in situations of securing an airway in an emergency. No methods of oxygenation and ventilation were designed for this apparatus in case of a patient's apnea, and thus the device is impractical for use in emergency situations.

McGrail (U.S. Pat. No. 4,584,998) discloses a multi-purpose tracheal tube, which can be used for high frequency ventilation, irrigation of airway and monitoring, and having three lumens provided in the tracheal tube. A major shortcoming of this design is that the opening of "insufflation lumen" is more than 5 cm away from the distal tip of tracheal tube, and the opening face the lumen, instead of pointing to the front. Thus, it would be difficult to use this "insufflation lumen" for generating powerful forwarding jet pulses for efficient oxygenation and ventilation if patients have apnea after receiving muscle relaxants. No $PetCO_2$ monitoring catheter or other kind catheters are provided to guide and assist tracheal inbutation blindly in a difficult airway. The device appears to be useful for cleaning airway secretion during mechanical ventilation without interruption of oxygenation and ventilation, but does not appear to be adequate for assisting intubation in paralyzing patients with difficult airway.

In sum, there is a continuing need for an intubation device and method that can be employed to intubate patients quickly and reliably, especially in unexpected emergency situations in which conventional intubation techniques cannot be employed. It is very important that some kind of oxygenation and/or ventilation be maintained during intubation so that the chance of hypoxia and hypercapnia is minimized and the allotted time for intubation be prolonged.

SUMMARY OF THE INVENTION

The present invention provides an endotracheal device having both a tube for delivering jet oxygen pulses during tracheal intubation and another tube for receiving a monitoring device. The monitoring device is used both to guide the endotracheal tube into the trachea and to facilitate intubation, which is especially important in intubation for patients with difficult airways.

It is an object of the present invention to provide an endotracheal device including an endotracheal unit or tube capable of using high-pressure oxygen pulse to maintain oxygenation and/or ventilation during endotracheal intubation. The endotracheal device includes a monitoring device, such as a catheter for monitoring end-tidal $CO_2$ ($PetCO_2$), positioned inside the lumen of the endotracheal unit, for use in assisting intubation in a difficult airway during jet ventilation.

The present invention provides an intubation device and technique for endotracheal intubation aimed at reducing the chance of hypoxia and hypercapnia and subsequent morbidity and mortality during endotracheal intubation. The intubation device and method will be especially helpful for emergency endotracheal intubation and for patients with difficult airways, such as in the cases of patients with trauma or pregnant patients who need immediate C-sections under general anesthesia.

Thus, the present invention advantageously provides an endotracheal device including an endotracheal unit comprising a first tube having a proximate end, a distal end, an anterior surface, and a posterior surface. The first tube wall encloses a first lumen having a cross-sectional area and having an exterior surface and an interior surface. The endotracheal device also includes a second tube having proximate end, a distal end, and a second tube wall enclosing a second lumen having a cross-sectional area. The second tube wall extends from the first tube wall, preferably the anterior exterior surface of the first tube wall. In addition, the cross-sectional area of the second lumen is smaller than the cross-sectional area of the first lumen. Further, the distal end of the second tube extends beyond the distal end of the anterior surface of the first tube.

Preferably, the endotracheal unit according further comprising an insufflation cuff positioned proximate the distal end of the first tube, and a third tube for inflating the insufflation cuff.

In addition, the endotracheal device of the present invention also includes at least one patient-monitoring device. The at least one patient monitoring device is preferably selected from (1) catheters for monitoring end-tidal $CO_2$, and (2) visual monitoring devices for observing the vocal cord. The at least one monitoring device is positioned in the lumen of the first tube of the endotracheal unit.

Further, the endotracheal device preferably further comprises a bendable, shape-retaining stylet for shaping the endotracheal device.

Preferably, the endotracheal device of the present invention also includes a source of jet ventilation for providing jet ventilation through the second tube.

The present invention also provides a method of intubation using an improved endotracheal device. The endotracheal device comprises an improved ET or endotracheal unit as described above, a jet device such as a jet ventilator being connected to the second tube of the endotracheal unit, and at least one patient-monitoring device. The at least one patient monitoring device is selected from the class consisting of (1) catheters for monitoring end-tidal $CO_2$, and (2) visual monitoring devices for observing the vocal cord. The at least one monitoring device is positioned in the lumen of the first tube of the endotracheal unit.

The method of intubation comprises (1) positioning the distal end of the second tube under the epiglottis of the patient while aligning the first tube with the midline of epiglottis; (2) starting jet ventilation via the second tube using the jet ventilator or other jet device, (3) adjusting the direction of the distal tip of the second tube as indicated by the monitoring device; (4) advancing the monitoring device into the trachea via passing the vocal cord opening while continuing jet ventilation; and then (5) sliding the endotracheal device over the monitoring device into the trachea.

In one presently preferred embodiment of the method of intubation of the present invention, the at least one monitoring device is an end-tidal $CO_2$ monitoring catheter, and the direction of the distal tip of the second tube is adjusted to obtain the maximum end-tidal $CO_2$, to achieve a capnogram with a stable plateau.

In another embodiment of the method of intubation of the present invention, the at least one monitoring device is preferably a visual monitoring device for observing the vocal cord, preferably a fiber-optic scope.

In the method of intubation of the present invention, it is preferred that the chest rise and breath sound of the patient on the exterior chest wall be monitored during the intubation process, and especially as an aide to guiding placement of the $PetCO_2$ monitoring catheter in the trachea.

Preferably, in the method of intubation of the present invention also includes shaping the endotracheal unit with a bendable, shape-retaining stylet.

In the method of intubation of the present invention, the monitoring device is preferably withdrawn from the jet endotracheal unit after the unit has been successfully positioned in the trachea.

Preferably, in the method of intubation of the present invention further includes discontinuing jet ventilation through the second tube, and providing ventilation to the patient through the first tube, after the endotracheal unit has been successfully positioned in the trachea.

Preferably, the method of intubation of the present invention further includes capping the proximate end of the second tube after the endotracheal unit has been successfully positioned in the trachea.

In one presently preferred embodiment, the method of intubation of the present invention further includes providing conventional ventilation to the patient through the first tube after the endotracheal unit has been successfully positioned in the trachea.

In another embodiment, the method of intubation of the present invention further includes providing jet ventilation to the patient through the first tube after the endotracheal unit has been successfully positioned in the trachea.

Preferably, in the method of intubation of the present invention, the endotracheal unit further comprises an inflatable insufflation cuff, and the method further includes inflating the insufflation cuff after the endotracheal unit has been slid into the trachea of the patient.

In another aspect, the present invention provides for the use of the second or jet tube or channel for removing secretions from the trachea by the application of suction and/or for the administration of medicine, without significantly affecting ventilation through the first tube of the endotracheal unit. In yet another aspect the present invention provides for use of the second tube to monitor $PetCO_2$ and/or airway pressure when the first tube is used for jet ventilation after endotracheal intubation has been accomplished.

The method of intubation of the present invention further optionally includes delivering medication to the patient through the endotracheal unit, and further optionally includes applying suction to the patient through the endotracheal unit.

HEADING

DETAILED DESCRIPTION

Based on experimental results obtained and described below, the endotracheal unit, device and method of the present invention provide the following advantages: The endotracheal unit and device of the present invention is simple and easy to use, even for the beginner without previous experience of tracheal intubation. Further, the endotracheal unit is not expensive and easily constructed using conventional materials. The endotracheal unit and device of the present invention provide adequate oxygenation and ventilation during the intubation even for patients with complete apnea, thus increase the safety of intubation. The endotracheal unit and device of the present invention provide easy and effective guiding methods for assisting the tracheal intubation blindly even at Grade III or IV view of glottis in a difficult airway. The endotracheal unit has been designed to minimize the intubation-associated complications, such as airway trauma, barotraumas and misplacement into the esophagus. The present invention provides for monitoring end-tidal $CO_2$ and/or airway pressure during jet ventilation. Finally, the present invention provides methods of medication administration and secretion removal from the trachea during mechanical ventilation.

Figure 1:
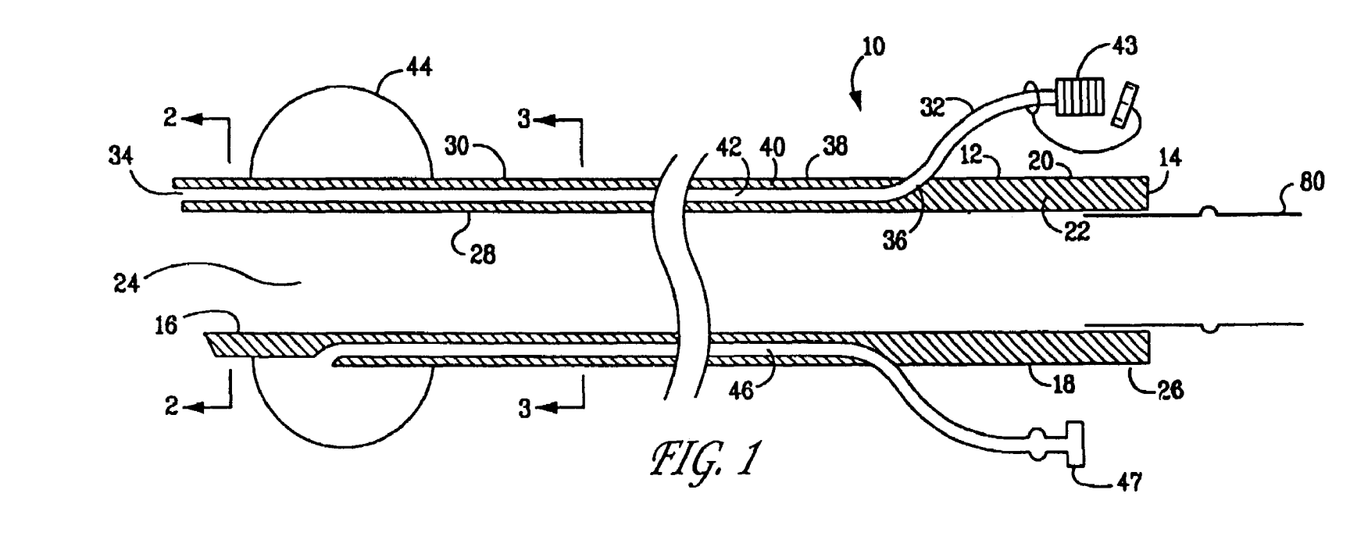
FIG. 1 is a schematic broken cross-sectional side elevational view of an endotracheal unit according to the present invention.

Referring now to the drawings in detail, wherein like reference numerals indicate like elements throughout the several views, there is shown in FIG. 1 a schematic broken cross-sectional side elevational view of an endotracheal unit ("ETU") 10 according to the present invention. The endotracheal unit 10 includes a first tube 12 having a proximate end 14 and a distal end 16, as well as a posterior surface 18 and an anterior surface 20, and a wall 22 surrounding an interior cavity or lumen 24 which extends the entire length of the first tube 12. The wall 22 of the first tube 12 has an exterior surface 26 and an interior surface 28 surrounding the lumen 24. An adapter 80 is fitted to the proximate end 14 of the first tube 12 for connecting the first tube 12 to conventional ventilation apparatus (not shown) after intubation has been completed.

The ETU is preferably constructed by a conventional plastic extrusion technique using a medical grade plastic material with a suitable balance of rigidity and flexibility to provide an ETU that can be easily manipulated for positioning within a patient's airway, yet with minimal patient discomfort or trauma.

"Anterior" is used with reference to the manner in which the endotracheal unit 10 is used during intubation of a patient (not shown), with "anterior" referring to the front or anterior of the patient's body. Thus, for example, the anterior surface 20 of the first tube 12 is that surface of the first tube 12 that is directed towards the anterior of the patient's body during intubation. Similarly, the posterior surface 18 is directed towards the posterior or rear of the patient's body during intubation. In like manner, the distal end 16 is the end of the tube 12 that is positioned within the patient's body during intubation, while the "proximate" end 14 of the tube 12 is the end that remains outside of the patient's body during intubation.

Figure 2:
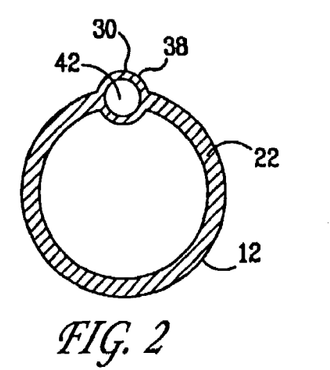
FIG. 2 is a cross-sectional front elevational view of the endotracheal unit of FIG. 1 taken along the line 2-2.

The endotracheal unit 10 also includes a second tube 30 having a proximate end 32 and a distal end 34, a wall 40 having a posterior surface 36 and an anterior surface 38, the wall 40 enclosing a cavity or lumen 42. The wall 40 of the second tube 30 extends from the anterior exterior surface 20 of the wall 22 of the first tube 12, as shown in the front elevational cross-sectional view of FIG. 2. The cross-sectional area of the first tube 12 is greater than the cross-sectional area of the second tube 30. Optionally, the second tube 30 can extend from elsewhere on the exterior surface of the first tube 12, such as for example, the posterior exterior surface (not shown), although this is presently less preferred.

Preferably, the second tube has an interior diameter of from about 1.6 mm to 2.3 mm.

Figure 6:
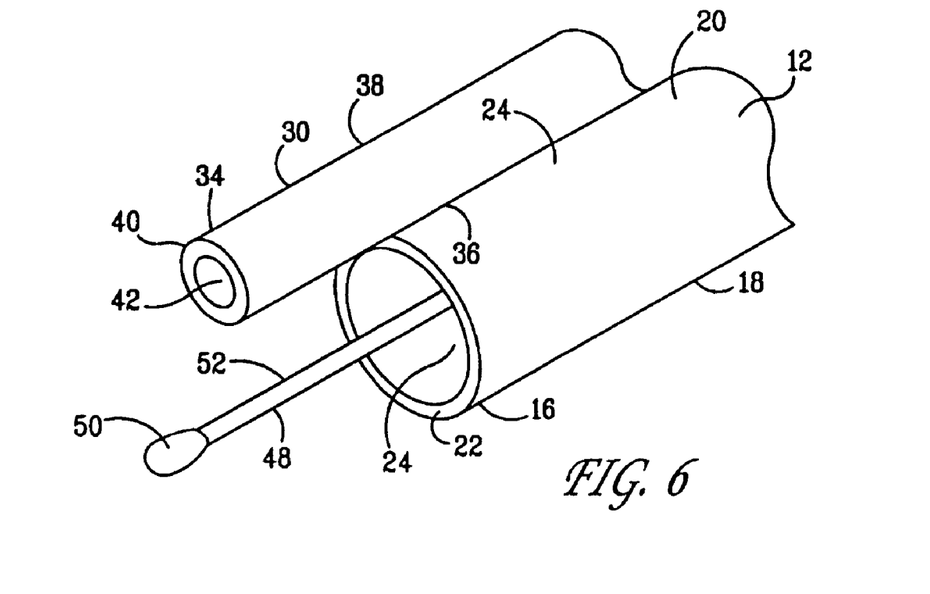
FIG. 6 is partial perspective view of the distal end of an alternative embodiment of an endotracheal device according to the present invention.

In the alternative embodiment of an endotracheal device according to the present invention shown in the partial perspective view of the distal end of FIG. 6, the distal end of the second tube is not continuous with the distal end of the first tube, but rather extends discretely beyond the distal end of the first tube. In this embodiment, the distal end of the second tube should not extend too far beyond the distal end of the first tube, or it will act like a single jet catheter and may increase the likelihood of intrusion into the pocket under vocal cord and cause barotrauma. However, it is presently believed that if the distal end of the second tube is not beveled and is soft (e.g. not formed of metal or a rigid plastic material) it may reduce the chance of the barotrauma.

The second tube 30 extends from the distal end of the endotracheal unit 10, but does not extend for the entire length of the endotracheal unit 10. Rather, the second tube 30 instead terminates in a fitting 43 for connecting the second tube 30 with a source of jet ventilation 70, such as a jet ventilator or other jet devices for producing jet ventilation with oxygen, shown schematically in FIG. 4. As best seen in the partial perspective views of alternative embodiments of the distal end of the endotracheal unit 10 shown in FIGS. 5 and 6, the distal end 34 of the second tube 30 extends beyond the distal end 16 of the anterior surface 20 of the first tube 12, providing the endotracheal unit with a beveled distal end. In use, the beveled distal end of endotracheal unit 10 faces down with respect to the patient, rather than facing left as in the use of a conventional endotracheal tube.

Figure 3:
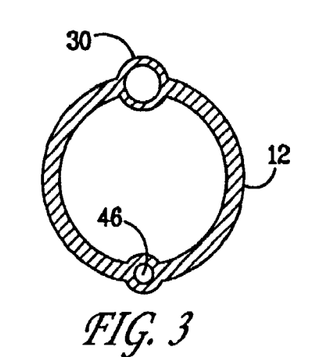
FIG. 3 is a cross-sectional front elevational view of the endotracheal unit of FIG. 1 taken along the line 3-3.

The endotracheal unit 10 also optionally includes an inflatable insufflation cuff 44 positioned near the distal end of the endotracheal unit 10 and surrounding the first tube 12 and second tube 30 for sealing the endotracheal unit 10 in the trachea after intubation. The insufflation cuff 44 is connected by a third tube 46 formed in the posterior of the wall 22 of the first tube 12 (best seen in the front elevational cross-sectional view of FIG. 3) to a fitting or inlet 47 for inflating the cuff 44 using a conventional technique, as with a syringe (not shown).

Figure 4:
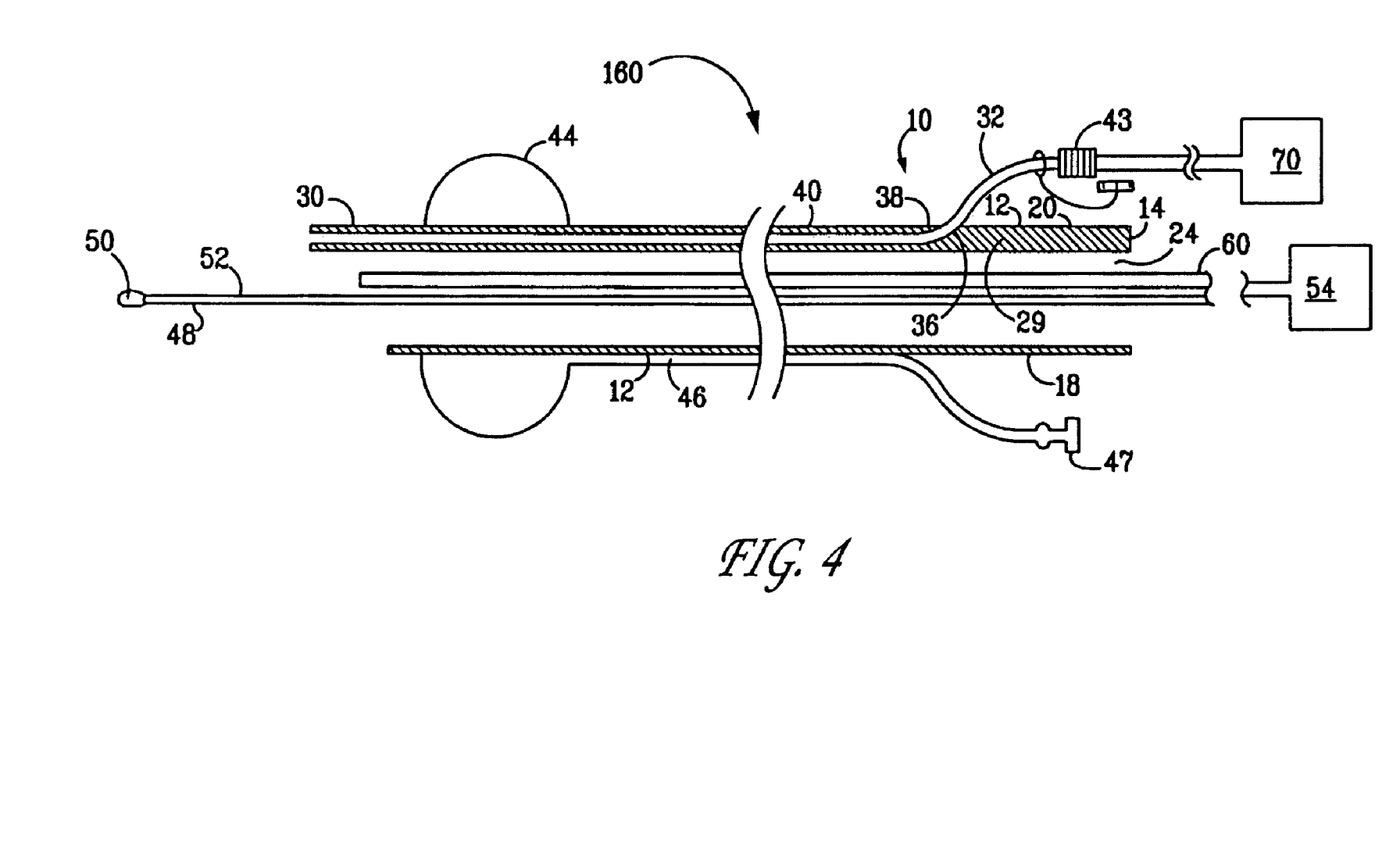
FIG. 4 is a schematic broken cross-sectional elevational view of an endotracheal device according to the present invention.

As shown in FIG. 4, a schematic broken cross-sectional elevational view of an endotracheal device 160 according to the present invention, the endotracheal device 160 includes the endotracheal unit 10, as well as at least one patient monitoring device 54, such as a catheter for monitoring end-tidal $CO_2$, or a visual monitoring device for observing the vocal cord. The at least one monitoring device 54 includes a catheter 48 and probe 50 at the distal end of the catheter 48. The catheter 48 of the monitoring device 54 is preferably positioned in the lumen 24 of the first tube 12 of the endotracheal unit 10. For example, a semi-rigid radiopaque polyurethane jet catheter having an interior diameter of from about 1.6 mm to 2.3 mm (depending on the lumen 24 of the first tube 12 of the endotracheal unit 10) can be placed inside the lumen 24 of the first tube 12 of the endotracheal unit 10, and can be used both for (1) monitoring $PetCO_2$ ($PetCO_2$ monitoring catheter), and (2) assisting intubation after the distal end of the catheter is placed inside the patient's trachea. In addition, a bendable, shape-retaining stylet 60 is disposed within the lumen 24 of the first tube 12 to aid in shaping, inserting and positioning the endotracheal unit 12 within the patient's airway.

The present invention also provides an improved method of performing intubation. In the present method, after induction of general anesthesia, a muscle relaxant is administered to the subject patient, and direct laryngoscopy with MAC or Miller blades is performed. If the whole glottis is visible as in a Grade I view, an endotracheal unit according to the present invention, fitted with a monitoring device and stylet, is placed into the trachea directly, just as in the case of intubation with a conventional endotracheal tube. At the same time, high-pressure oxygen is delivered to the trachea as a jet pulse through the second tube or jet channel in the anterior wall of the endotracheal unit only as necessary to maintain oxygenation. Then, the monitoring device, such as a $PetCO_2$ monitoring catheter, and the stylet inside the lumen of endotracheal unit are removed. The proximal opening of the second tube on the endotracheal unit is closed after proper placement of the endotracheal unit, and CMV or HFJV can be started using the endotracheal unit as a conventional endotracheal tube. In addition, the proximal end of the second tube of the endotracheal unit can be connected to a suction to remove secretion inside the trachea. If the jet ventilation is chosen, the proximal end of the second tube in the anterior wall of the endotracheal unit can be used to monitor $PetCO_2$ or airway pressure continuously.

If only posterior part of glottis (Grade II view) or the tip of the epiglottis (Grade III view) is visible, an oral gastric tube is recommended to be first inserted into the esophagus and connected to a constant suction to prevent possible gastric distension and associated barotraumas during the use of jet ventilation. Then, the distal tip of the endotracheal unit is placed under the epiglottis, with its midline of the endotracheal unit and the epiglottis aligned. As jet pulses of oxygen are being delivered through the second tube in the endotracheal unit from a jet ventilator or other jet device, the patient is monitored using the patient-monitoring device, such as a $PetCO_2$-monitor. In addition, chest rise and breath-sound of the right front chest are preferably also monitored in a conventional manner. The direction of the distal end of the endotracheal unit is then adjusted while the patient is monitored to obtain an optimum orientation. For example, the direction of the distal end of the endotracheal unit can be adjusted to maximize $PetCO_2$ with a stable plateau on the capnogram and chest rise and breath sound. This can be observed when the distal tip of the second tube of the endotracheal tube is pointed directly to the glottis opening, and jet pulses of oxygen are maximally delivered into the trachea.

After the tip of the endotracheal unit is aligned with the trachea, and the tip of the second tube of the endotracheal unit is directed to the opening of glottis by preferably all but at least one of the above-described methods, the monitoring catheter inside the lumen of the first tube of the endotracheal unit is gently inserted into trachea to about 8-10 cm below the vocal cord, as indicated by a marked number on the monitoring catheter. If there is resistance to placing the monitoring catheter, the distal end of endotracheal unit can be changed slightly to the left or the right until the monitoring catheter can be easily placed into the trachea. Preferably, chest rise and breath sound on the right front chest are constantly monitored so that the monitoring catheter will be kept in the pathway going into the trachea, but not the esophagus. If the monitoring catheter is adapted to means $PetCO_2$, this quantity is also monitored. If the monitoring catheter is provides a visual indication, the direction of the tip of the endotracheal unit can be adjusted responsively. When the distal end monitoring catheter is 8-10 cm below the vocal cord, and is confirmed to be inside trachea, for example, by the monitored level or $PetCO_2$, by direct visual indication, and/or by the monitored chest rise and breath sound on the right front chest, the endotracheal unit is then slid over the monitoring catheter into the trachea. Thereafter, the endotracheal unit is confirmed to be inside the trachea and, and the endotracheal unit is then used for either CMV or jet ventilation as described above.

When only soft palate is viewed (Grade IV view), the distal tip of the endotracheal unit is first placed close to the glottis under a MAC or Miller blade, with the midline of an endotracheal unit and the midline of the patient's head aligned. As with a Grade III view situation, after initiating the jet ventilation using the second tube of the endotracheal unit and jet ventilator, the direction of the distal end of endotracheal unit is adjusted in response to the patient-monitoring device. For example, the direction of the distal end of the endotracheal unit can be adjusted so that the maximum value of $PetCO_2$ with a stable plateau on the capnogram, and maximum chest rise and breath sound, can be observed. Thereafter, the endotracheal unit is placed into the trachea as in the procedures described above.

The endotracheal unit and device of the present invention have several major advantages compared to conventional endotracheal tubes. First, the jet pulses delivered through the second tube of the endotracheal unit can maintain oxygenation and/or ventilation during intubation, which alternatively prolongs the allotted time for intubation and reduces the incidence of morbidity and mortality secondary to hypoxia and hyercapnia during trachea intubation. Secondly, the monitoring catheter positioned inside the lumen of the first tube of the endotracheal unit can be used for both monitoring the patient (for example, monitoring the patient's $PetCO_2$), and to assist positioning the endotracheal unit in the trachea. This will help with an otherwise "blind" intubation during the difficult airway with views of glottis of Grade III and IV, and obviously speeds the tracheal intubation in a difficult airway. Thirdly, the second tube built in the anterior wall of an endotracheal unit can also be used for suction and/or medication administration during both CMV and jet ventilation, as well as for monitoring of $PetCO_2$ and airway pressure during the jet ventilation.

The endotracheal unit and device of the present invention are useful for tracheal intubation with all kinds of patients to improve the safety of the process. However, the present invention is especially useful and valuable for tracheal intubation in an emergency situation, such as in cardiopulmonary resuscitation, acute respiratory failure, trauma, emergent cesarean section under general anesthesia etc. The present invention will also be especially valuable for tracheal intubation for patients with an unexpectedly difficult airway, especially for those with Grade III and IV view of glottis.

The efficiency and detection of possible complications of endotracheal units and devices of the present invention were tested in studies in intubation of ten adult pigs. The efficiency of jet ventilation using the devices and units of the present invention to maintain adequate oxygenation and ventilation during the intubation and the efficiency of three methods to guide tracheal intubation with an endotracheal unit of the present invention was studied. Possible complications, such as barotraumas and airway edema, were also studied.

Materials and Methods

Animals and Anesthesia:

All animal experiment protocol were reviewed and approved by IACUC at the University of Pennsylvania. Ten male adult pigs weighing 52.4 to 62 kg was anesthetized initially with a mixture of ketamine (25 mg/kg), xylazine (2 mg/kg), glycopyrolate (0.02 mg/kg), IM. Adjunct analgesia was provided with buprenorphine (0.05 mg/kg) IM. Thereafter, pigs were placed on an operating table in a supine position. A G20 angiocatheter was placed in one of the ear veins for intravenous anesthetics and fluids. Another G20 angiocatheter was placed in right femoral artery to monitor systolic arterial pressure (SAP) and diastolic arterial pressure (DAP), and for collecting blood sample for arterial blood gas (ABG) analysis. Multiple leads ECG, rectal temperature (Temp), oxygen saturation ($SaO_2$) and end-tidal $CO_2$ (PetCO2) were also monitored and recorded periodically. General anesthesia was maintained with alpha-chloralose at a loading dose of 50 mg/kg, IV and then a maintaining dose of 10 mg/kg IV every half-hour. Pilot studies have shown that this dose of alpha-chloralose will maintain pigs pain free from toe pinches. Atropine will be given as necessary to increase heart rate closing to the baseline level (0.02 mg/kg IM and then ⅕ to ¼ dose IV as needed). Intravenous normal saline was given as needed to maintain normal blood pressure.

Endotracheal units (ETU) and devices to produce jet pulses for jet ventilation:

A prototype endotracheal unit (ETU) was constructed from a plastic tube with ID of 2.4 mm which was fixed to the outside of the anterior or posterior wall of a regular endotracheal tube (ET). A tube exchanger (TE) from Cook Critical Care (Bloomington. Ind.) with ID of either 1.6 mm or 2.3 mm was placed within the plastic tube with its distal tip parallel to the distal tip of the ET, and used as a jet catheter. Another tube exchanger with ID of 2.3 mm (Cook Critical Care) was placed inside lumen of the regular ET and connected to a $PetCO_2$ monitor. A regular metal stylet was also placed inside the lumen of the ET to shape the ET to an about 30-degree L-shape.

Three devices were used to produce jet ventilation in this experiment: The first was a commercially available manual jet ventilator. Jet ventilation was produced by high-pressure oxygen flow passing through a valve intermittently to produce jet pulse. The ventilating settings used were a driving pressure of 15 psi, a breathing rate of 15/minute, and an I/E ratio of 1:1. The second device is a commercially available Enk oxygen flow modulator (Cook Critical Care) to produce jet ventilation with a regular wall oxygen outlet, that can provide oxygen flow 15 liter/min. The third device was a self-made jet device composed of a transport breathing circuit, #7 ET adapter and 3 ml syringe. The transport circuit tube was connected to a wall oxygen outlet. With a thumb blocking the big outlet of the breathing circuit intermittently, jet ventilation can be produced. The ventilation setting we used for both Enk oxygen modulator and self-made breathing circuit jet device were the same (oxygen flow rate: 15 liter/minute, breathing rate: 15/minute, I/E ratio 1:1). The ETU could be connected to any of the three devices described above to produce jet ventilation.

Experimental Protocols

A. Efficiency of jet ventilation with two different sizes of jet catheters and three different jet ventilation devices using the self-made jet ET prototype.

First, baselines of ABG, $SaO_2$, hemodynamic variables (SAP, DAP, HR), rectal temperature, chest rise degree (0=none, 5=maximum chest rise), breath sound on the right front chest (BS-FC), the front trachea midline (BS-FT) were monitored and recorded during spontaneous breathing (SB). The intensity of breath sound on the right front chest during spontaneous breathing is considered a reference number of one and the breath sound intensity in all other situation will be quantified according to this reference number. Thereafter, pancuronium at 0.2 mg/kg was given intravenously to paralyze the pigs and then given IV continuously with an IV pump at 20 mg/hr to maintain the muscle trains of four (TOF) twitches at post titanic facilitation (PTF) or zero. Immediately after paralyzing pigs, jet ventilation with a Big TE was initiated with its distal tip about 45 degree deviated from the vocal cord opening. The time of $SaO_2$ to drop to 80% from baseline was recorded and an ABG was obtained at this time. The pigs were then intubated with the distal tip of the jet ET 4 cm below vocal cord (VC). Jet ventilation was initially performed with manual jet ventilator using a small ID (1.6 mm) tube exchanger (Small TE Jet) for 20 min, which was then replaced with a big ID (2.3 mm) TE (Cook Critical Care, Big TE Jet). Jet ventilation was produced with one of the three jet devices described above in random. ABG, and all other monitoring variables mentioned above were recorded after jet ventilation with each device for 20 min. Thereafter, the jet ET was pulled out and its distal tip was placed above vocal cord and facing directly the opening of the vocal cord. Similarly as in the experimental protocol of using jet ET inside trachea, efficiency of jet catheters using small or big ID (1.6 mm vs. 2.3 mm, Small vs. Big TE Jet) tube exchanger by manual jet ventilator and the ventilation setting described above was compared. Also, the efficiency of three described jet devices using the big jet catheter (ID 2.3 mm, Big TE circuit and Big TE Enk) was also compared after 20 min of jet ventilation for each device.

B. Efficiency of ETU in difficult airway intubation:

With the pigs paralyzed, the efficiency of three methods ($PetCO_2$, chest rise and breath sound) in guiding the distal tip of the ETU to pass through vocal cord "blindly" (i.e. without visual observation) and in a difficult airway to achieve complete intubation was compared. The difficult airway was simulated by pretending to be unable to lift epiglottis and view vocal cord when doing direct laryngoscopy. The tip of the ETU was placed under the epiglottis with its midline aligned with the midline of epiglottis. The pointing direction of the distal tip of the jet catheter was changed until the maximum $PetCO_2$ with a stable plateau on the capnogram, chest rise and the breath sound were detected. The jet catheter or the $PetCO_2$ monitoring catheter was then inserted into the trachea blindly. The jet ventilation was continued and the chest rise, $PetCO_2$ and breath sound were constantly monitored to make sure the jet catheter or $PetCO_2$ monitor catheter was kept in the pathway into the trachea, rather than esophagus, during its insertion. The ease and the success rate of placing either the jet catheter or the $PetCO_2$ monitoring catheter was noted and compared. After placing the jet catheter or the $PetCO_2$ monitoring catheter about 8-10 cm below the vocal cord by checking the marked number on the TE catheters, the ETU was slid over the stabilized jet catheter or $PetCO_2$ monitoring catheter into the trachea. The easiness or successful rates of sliding the ETU over two different catheters were compared. Different lab technicians without intubation experience would repeat the intubation procedures with the ETU, and their success rates on intubation were compared to that of an experienced anesthesiologist. In this way, the ease with which beginners can learn this new technique could be assessed.

C. Comparison of efficiency using jet catheter and $PetCO_2$ monitoring catheter.

Using a tube exchanger with ID of 2.3 mm as a jet catheter and $PetCO_2$ monitoring catheter, the success rate of passing either catheter over the vocal cord opening and sliding the jet ET over either catheter was compared. The final success rate of each pig was the average of three separate operators, with each operator testing both catheters of minimum of three times.

D. Comparison of jet pulse located in anterior or posterior wall of the jet ET.

The success rate of facing the vocal cord opening when the distal tip of the jet ET was placed under glottis the first time and the success rate of passing the $PetCO_2$ monitoring catheter over the vocal cord opening was compared when the jet catheter is located in anterior or posterior wall of a regular ET. The final success rate of each pig was the average of three separate operators, with each operator testing both position of jet catheter at minimum of three times.

E. Complications and the ETU.

During the experiments, the possible complications experienced with the ETU, such as barotraumas (pneumothorax, air in the neck soft tissue or mediastinum, etc.), airway trauma and edema and any other obvious abnormal finding were monitored, recorded and compared among different jet devices. Possible ways to prevent complications were also assessed. For example, whether the NG tube could prevent stomach distension caused by jet ventilation was studied.

F. Statistical Analysis.

Statistical analyses of the results were obtained as follows. ANOVA followed by multiple comparison tests was used for the tests in protocols A and B. The Student t-test was used for analyzing the data in the protocols C and D.

Results

A. The efficiency of jet ventilation using different size of tube exchanger (ID 1.6 mm vs. 2.3 mm) as jet catheters and three different jet devices was measured when the tip of the ETU is 4 cm below the vocal cord.

Table 1 and Table 2 summarize the changes of different monitoring variables during use of two sizes of jet catheters and three kinds of jet devices. In Table 1, there are no significant differences in hemodynamic variables (SAP, DAP, HR) and rectal temperature among baseline and jet ventilations with all three different jet devices. For the ABG, the pH of big TE Jet was significantly higher than others except baseline, probably caused by the decreased $PaCO_2$. $PaO_2$ of jet ventilation with any kind of jet device is significantly higher than baseline because we used the 100% oxygen as driving gas. In addition, $PaO_2$ in the Big TE Jet is also significantly higher than that of the Big TE Enk. There were no significant differences among all other ABG variables. In Table 2, the chest rise in the Big TE Jet is significantly higher than that in the Big TE circuit and Enk. Also, the breath sound on right front chest (BS-FC) and front trachea (BS-FT) with Big TE Jet were significantly higher than baseline and all other jet devices.

compared to all others. "e" means $P<0.05$ compared to others except Big TE Circuit.

B. The efficiency of jet ventilation using two sizes of Cook tube exchanger as jet catheters and three different jet devices was measured when the tip of jet ET was directly above and facing the vocal cord opening or 45° to the right of the vocal cord opening.

As shown in table 3, $PaCO_2$ in the Big TE jet 45° to right was significantly increased over the baseline, Small TE and

TABLE 1

|  | Baseline | Small TE Jet | Big TE Jet | Big TE Circuit | Big TF Enk |
|---|---|---|---|---|---|
| SAP | 128 ± 5.5 | 124 ± 2.5 | 120 ± 4.5 | 117 ± 4.6 | 123 ± 4.1 |
| DAP | 83 ± 2 | 83 ± 3.6 | 84 ± 3.6 | 80 ± 7 | 81 ± 3.9 |
| HR | 84 ± 4.4 | 80 ± 5 | 88 ± 5 | 77 ± 4.6 | 67 ± 9 |
| TEMP | 99.2 ± 0.27 | 98 ± 0.4 | 98.7 ± 0.4 | 98 ± 0.4 | 98 ± 0.36 |
| pH | 7.46 ± 0.025 | 7.42 ± 0.04 | 7.55 ± 0.04[a] | 7.416 ± 0.03 | 7.378 ± 0.04 |
| $PaCO_2$ | 39.9 ± 0.9 | 47 ± 5.3 | 35.6 ± 3.7 | 47 ± 4.8 | 55 ± 6.3 |
| $PaO_2$ | 88.6 ± 4.9[b] | 327 ± 45 | 456 ± 37[c] | 357 ± 32 | 285 ± 35 |
| $HCO_3$ | 27 ± 1.9 | 21 ± 2.5 | 26 ± 3.8 | 28 ± 2 | 28 ± 1.3 |
| $SaO_2$ | 98.8 ± 0.3 | 99.6 ± 0.12 | 99.6 ± 0.6 | 99.6 ± 0.2 | 99.6 ± 0.3 |

Table 1 provides comparative studies of monitored variables among different jet devices with the distal tip of #7 jet endotracheal tube 4 cm below vocal cord. The reported data represents mean±SE of ten separate experiments. "TE" means tube exchanger from Cook Critical Care. The ID of the "Small" and "Big TE" are 1.6 mm and 2.3 mm respectively. "a" means $P<0.05$ compared to all others except baseline. "b" means $P<0.05$ compared all others. "c" means $P<0.05$ compared to the Big TE Enk.

Big TE Jet. $PaO_2$ in the Big TE Jet 45° to right significantly decreased compared to jet ventilation using any kind of jet device but not the baseline. $SaO_2$ in Big TE Jet 45° to right was significantly lower than all others. No significant changes could be detected in any of the hemodynamic variables (SAP, DAP, HR), rectal temperature and other ABG variables. As shown in table 4, the $PetCO_2$, chest rise and breath sound in the right front chest (BS-FC) in Big TE Jet 45° to right were significantly lower than baseline or any

TABLE 2

|  | Baseline | Small TE Jet | Big TE Jet | Big TE Circuit | Big TF Enk |
|---|---|---|---|---|---|
| $PetCO_2$ | 40 ± 0.9 | 47 ± 5 | 36 ± 3.7 | 48 ± 5 | 55 ± 6.3 |
| Chest Rise | 2.6 ± 0.12[a] | 2.07 ± 0.35 | 3.4 ± 0.16[b] | 1.78 ± 0.26 | 1.5 ± 0.25 |
| BS-FC | 0.99 ± 0.001 | 1.21 ± 0.17 | 1.79 ± 0.17[c] | 0.57 ± 0.07 | 0.7 ± 0.11 |
| BS-FT | 2.65 ± 0.35 | 2.78 ± 0.7 | 3.4 ± 0.2[d] | 1.87 ± 0.2 | 1.74 ± 0.18[e] |

Figure 5:
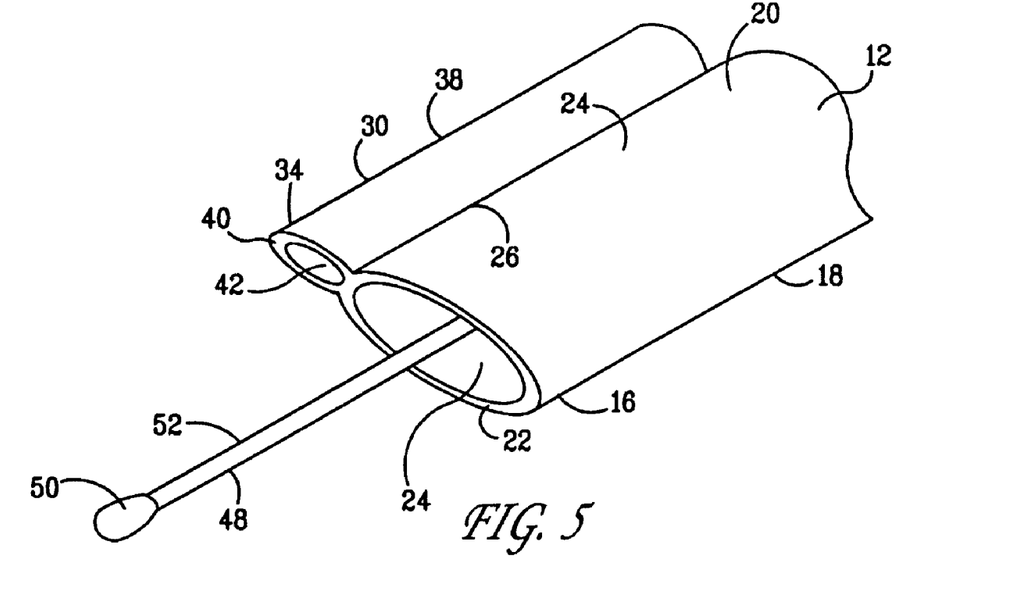
FIG. 5 is a partial perspective view of the endotracheal device of FIG. 4 showing the distal end of the device.

Table 2 provides an efficiency study of methods to detect the tip of #7 jet endotracheal tube inside the trachea using different jet devices and catheters. The tip of the jet endotracheal tube was 4 cm below vocal cord. The data presented represents mean±SE of ten separate experiments. "TE" means tube exchanger from Cook Critical Care. The ID of the "Small" and "Big TE" are 1.6 mm and 2.3 mm respectively. "a" means $P<0.05$ compared to Big TE Circuit and Big TE Enk. "b" means $P<0.05$ compared to all others. "c" means $P<0.01$ compared to all others. "d" means $P<0.05$ other mode of jet ventilation. The difference could be as high as 20 to 30 times for $PetCO_2$, chest rise. The breath sound in front trachea (BS-FT) in the Big TE Jet was significantly higher than baseline and other jet ventilation except Big TE Jet 45° to right. In FIG. 5, we compared the efficiency of $PetCO_2$, chest rise and breath sound on the right front chest (BS-FC) as methods to differentiate if the tip of jet ET is directly facing the vocal cord opening or 45° to the right. There are significant differences in both $PetCO_2$ and chest rise when comparing the distal tip of jet ET facing directly or about 45° to the right of the vocal cord opening.

TABLE 3

|  | Baseline | Small TE Jet | Big TE Jet | Big TE Circuit | Big TE Enk | Big TE Jet 45° to Right |
|---|---|---|---|---|---|---|
| SAP | 128 ± 5.5 | 117 ± 6 | 113 ± 3 | 130 ± 6.4 | 129 ± 6.7 | 127 ± 5.4 |
| DAP | 85 ± 2.8 | 84 ± 5.1 | 81 ± 4.7 | 85 ± 3.1 | 87 ± 7.4 | 83 ± 5.7 |
| HR | 88 ± 4.5 | 84 ± 7 | 84 ± 5.9 | 73 ± 5.1 | 86 ± 0.3 | 95 ± 11 |
| TEMP | 99.3 ± 0.3 | 97.8 ± 0.5 | 99 ± 0.42 | 98 ± 0.4 | 98 ± 0.4 | 97.9 ± 0.36 |
| pH | 7.46 ± 0.03 | 7.45 ± 0.03 | 7.42 ± 0.05 | 7.33 ± 0.08 | 7.27 ± 0.08 | 7.22 ± 0.07 |
| $PaCO_2$ | 44 ± 4.2 | 44 ± 7.9 | 41.7 ± 3.5 | 64 ± 11 | 77 ± 15 | 90 ± 17[a] |
| $PaO_2$ | 88.6 ± 4.9[b] | 265 ± 48 | 334 ± 31 | 343 ± 86 | 302 ± 62 | 58 ± 9.4[c] |
| $HCO_3$ | 28 ± 2.1 | 30 ± 2.8 | 30 ± 1.5 | 31 ± 2.6 | 33 ± 2.3 | 35.5 ± 1.9 |
| $SaO_2$ | 99 ± 0.1 | 99.4 ± 0.2 | 99.5 ± 0.2 | 99.4 ± 0.2 | 99.1 ± 0.17 | 74.4 ± 4.9[d] |

Table 3 provides a comparative study of monitored variables among different jet devices with distal tip of the #7 jet endotracheal tube above the vocal cord and facing directly the vocal cord opening. The distal tip of the jet endotracheal tube was under the epiglottis and either directly above or 45° to the right of the vocal cord opening. The reported data represents mean±SE of ten separate experiments. "TE" means tube exchanger from Cook Critical Care. The ID of the "Small" and "Big TE" are 1.6 mm and 2.3 mm respectively. "a" means P<0.05 compared to Baseline, Small TE Jet and Big TE Jet. "b" means P<0.05 compared to Big TE Jet, Circuit and Enk. "c" means P<0.05 compared to others except baseline. "d" means P<0.01 compared to all others.

TABLE 4

|  | Baseline | Small TE Jet | Big TE Jet | Big TE Circuit | Big TE Enk | Big TE Jet 45° to Right |
|---|---|---|---|---|---|---|
| $PetCO_2$ | 51 ± 3 | 54 ± 4.9 | 49 ± 7.1 | 61 ± 6.4 | 61 ± 9.8 | 2.7 ± 1.6$^a$ |
| Chest Rise | 2.57 ± 0.13 | 2.3 ± 0.25 | 2.5 ± 0.2 | 1.5 ± 0.2 | 1.18 ± 0.2$^b$ | 0.03 ± 0.01$^c$ |
| BS-FC | 1 ± 0.002 | 0.9 ± 0.04 | 1.24 ± 0.17$^d$ | 0.93 ± 0.18 | 0.65 ± 0.11 | 0.3 ± 0.1$^e$ |
| BS-FT | 2.65 ± 0.12 | 3.1 ± 0.27 | 4 ± 0.2$^f$ | 2.35 ± 0.12 | 2.2 ± 0.18 | 3.5 ± 0.5 |

Table 4 reports the results and a study of the efficiency of methods to detect the distal tip of #7 jet endotracheal tube facing the vocal cord opening using different jet devices. The distal tip of jet endotracheal tube was under epiglottis and directly above or 45 degrees to right of the vocal cord opening. The data reported represents mean±SE of ten separate experiments. "TE" means tube exchanger from Cook Critical Care. ID of the "Small" and "Big" TE are 1.6 mm and 2.3 mm respectively. "a" means P<0.001 compared to all others. "b" means P<0.01 compared to others except Big TE Circuit. "c" means P<0.01 compared to all others. "d" means P<0.05 compared to Big TE Enk. "e" means P<0.05 compared to all others. "f" means P<0.05 compared to others except Big TE Jet 45 degrees to right.

Figure 7:
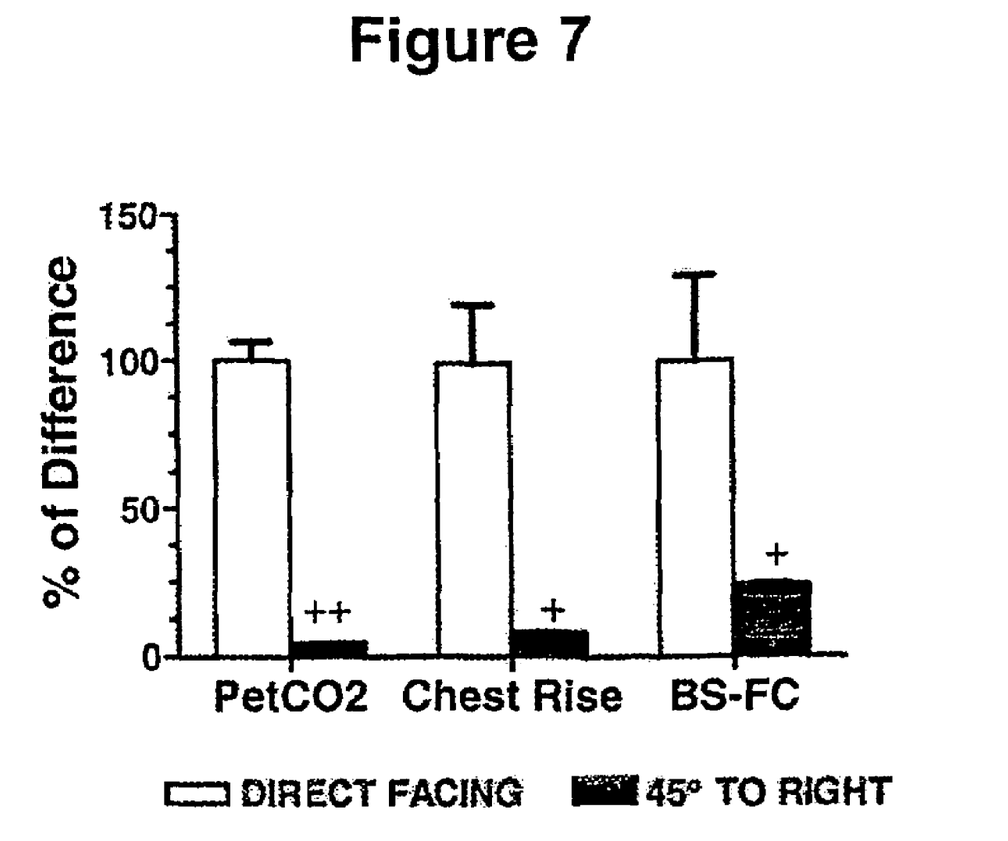
FIG. 7 is a graph providing a comparison of the efficiency of three methods to guide jet endotracheal tube into the trachea in difficult airways.

FIG. 7 provides a comparison of the efficiency of three methods to guide jet endotracheal tube into the trachea in difficult airways.

"BS-FC" means breath sound at the right front chest. "+" and "++" indicate P<0.05 or P<0.01 respectively comparing to the tip of jet endotracheal tube directly above and facing the vocal cord opening.

C. The success rate of passing a jet catheter or a $PetCO_2$ monitoring catheters (both are the tube exchangers with ID of 2.3 mm from Cook Critical Care) through the vocal cord opening was also assessed.

When both the $PetCO_2$ and the chest rise were maximized, and thus indicated that the distal tip of the jet ET was facing directly to vocal cord opening, there was a greater rate of success in passing the $PetCO_2$ monitoring catheter through the vocal cord opening than the TE jet catheter (Table 5, 88% vs. 69%, P<0.05). In addition, the jet ET was more easily and successfully slid over the $PetCO_2$ monitoring catheter than over the TE jet catheter (Table 5, 100% vs. 70%, P<0.01). It appeared that there were no significant differences in success rate to intubate jet ET between an anesthesiologist who had considerable experience on intubation and a lab technician who had no previous intubation experience.

TABLE 5

|  | Jet Catheter | $PetCO_2$ Catheter | P Value |
|---|---|---|---|
| Successful rate passing vocal cord opening | 68.7 ± 4.8 | 88 ± 5.8 | P = 0.027, N = 6 |
| Successful rate for jet ET sliding over the catheter | 70 ± 0.2 | 99.8 ± 0.2 | P = 0.007, N = 5 |

Table 5 provides the results of comparative studies of jet catheter and $PetCO_2$ monitoring catheter. Both catheters are tube exchangers with ID of 2.3 mm from Cook Critical Care. The jet catheter is located in a channel next to the posterior wall of a #7 regular endotracheal tube.

D. As shown in Table 6, there is a significantly higher successful rate of passing the $PetCO_2$ monitoring catheter through vocal cord opening when jet catheter is located on anterior wall of jet ET rather than on the posterior wall of jet ET (93% vs. 59%, P<0.01). However, there is no significant difference for successful rate of facing the distal tip of jet ET directly to vocal cord opening when the distal tip was placed under epiglottis and align with its midline at the first time.

TABLE 6

|  | Anterior Jet Channel | Posterior Jet Channel | P Value |
|---|---|---|---|
| Successful rate facing vocal cord opening first time | 80 ± 6.7 | 75 ± 10 | P = 0.7, N = 4 |
| Successful rate for $PetCO_2$ Monitoring catheter passing vocal cord opening | 93 ± 5.5 | 59.4 ± 9.9 | P = 0.008, N = 8 |

Table 6 provides the results of comparative studies of employing an anterior jet tube or channel versus a posterior jet tube or channel. Jet catheters are tube exchangers with ID of 2.3 mm from Cook Critical Care. The jet catheter is located in a channel next to the anterior or posterior wall of a #7 regular endotracheal tube.

E. When a pediatric fiber-optic cable replaced the $PetCO_2$ monitoring catheter in the lumen of a jet ET, the efficiency of placing a jet catheter into the trachea is less than using the method of placing $PetCO_2$ monitoring catheter, because it was difficult to control the distal tip of the fiber-optic cable so that it was facing the vocal cord opening quickly. It appeared to take more time to intubate the pigs using fiber-optic cable, than the $PetCO_2$ monitoring catheter.

F. Complication. Two of ten pigs developed severe barotraumas when using a single Frova jet catheter (Cook Critical Care) and a metal jet catheter with its distal tip angled as in Frova jet catheter but none with the jet endotracheal tube. This was demonstrated as significant neck distension secondary to the significant air in the soft tissue of neck. Autopsy of the pig with severe neck barotrauma demonstrated that the neck barotraumas happened only when the distal tip of angled distal tip of a single jet catheter (either Frova or metal jet catheter) was inserted into a pocket right below the vocal cord on either side. It is difficult for jet ET to be placed into this pocket because its broad distal tip prevents its intruding into the pocket.

Two of ten pigs developed moderate gastric distension, and the insertion of an OG tube resolved the gastric distension.

Four of ten pigs developed moderate swelling of epiglottis and throat after about 2 hr repeated intubations and significant manipulation of airways. However, a #6 jet ET could still be easily passed at the end of experiments for all pigs. Dexamethasone at 1 mg/kg seems to reduce the throat swelling significantly.

Conclusions

A. Efficiency of oxygenation and ventilation by jet ventilation using two different sizes of jet catheters and three different jet ventilation devices.

1. When the distal tip of the jet endotracheal tube was placed 4 cm below the vocal cord or was placed under epiglottis and was directly above and facing the opening of the vocal cord, jet ventilation (driving pressure of 15 psi, breathing rate of 15/minute and I/E ratio of 1:1) using jet catheters at ID of either 1.6 mm or 2.3 mm was sufficient to maintain the oxygenation and ventilation. Similarly using the TE at ID of 2.3 mm as a jet catheter, the self-made breathing circuit jet device and Cook Enk flow oxygen modulator (both at oxygen flow rate of 15 liter/min, breathing rate of 15/minute and I/E ratio of 1:1) provides adequate oxygenation and efficient ventilation. However, when the jet ET tip was directly above and pointing to the vocal cord opening, the self-made breathing circuit jet device and Cook Enk flow oxygen modulator could not provide sufficient ventilation, although they still provide adequate oxygenation.

2. When the tip of the jet endotracheal tube was placed under epiglottis and was about 45° deviated to the right of the vocal cord opening, jet ventilation provided insufficient oxygenation and ventilation. Interestingly, the $SaOP_2$ could still be maintained at 80% even after 20 mm apnea, although the $PaCO_2$ was significantly increased from 40 to 126 mm Hg.

3. It seems manual jet ventilator was a better choice than the self-made jet device or Enk oxygen flow modulator from Cook Critical Care because the former provided both adequate oxygenation and ventilation when the tip of the jet ET is above the vocal cord opening. However, in emergency situation, the later two devices used to generate jet ventilation are valuable to prevent hypoxia and help intubation in a difficult airway, although there may be chances of moderate hypercapnia after 20 minutes of use of this device.

4. The Big TE jet catheter (ID 2.3 mm) was more efficient than the small jet catheter (ID) in providing adequate oxygenation and ventilation and in assisting the distal tip of jet ET facing directly to vocal cord opening, and subsequent insertion of $PetCO_2$ monitoring catheter blindly. In addition, the large ID of the jet catheter also makes it more efficient for medication administration and suction of secretion. However, the large ID of jet catheter will occupy more space of the lumen of endotracheal tube and affect pathway of expiratory gas. The ID of the jet catheter should be smaller than 2.3 mm if the ID of jet ET is smaller than 8 mm for maintaining adequate expiratory pathway.

B. Efficiency of three methods to differentiate the tip of the jet ET facing directly to the vocal cord opening or to its side and the efficiency of the jet ET to be used in the difficult intubation.

1. $PetCO_2$ monitoring, chest rise and breath sound on the right front chest all can be used to differentiate if the tip of the jet ET is facing directly to the vocal cord opening or to its side. However, $PetCO_2$ monitoring and chest rise seemed to be better than the breath sound in this regard as the difference in the former two is about 20-30 times and only 5 times in the later method. In addition, it was difficult for the operator to listen the breath sound with a stethoscope when using the direct laryngoscope for intubation.

2. It was easier and more successful to place the $PetCO_2$ monitor catheter inside lumen of the jet ET than the jet catheter originally designed within a channel on the back of the jet ET. In addition, there is a higher success rate in passing the $PetCO_2$ monitor catheter through vocal cord opening when the jet catheter was located on anterior wall rather than on posterior wall. Further, it was easier and more successful to slide the ETU over the $PetCO_2$ monitor catheter than the jet catheter.

These results suggest substituting providing jet ventilation directly through the second tube of the ETU instead of using a separate jet catheter within that second tube, and that the second tube be located on or in the anterior wall of the ETU, rather than the posterior wall. The $PetCO_2$ monitor catheter, instead of separate jet catheter, is then placed into the trachea first and then the jet ET is slid over $PetCO_2$ monitor catheter into the trachea. This modification permits significantly decreasing the ID of the jet catheter channel and reducing the ratio of interior diameter and cross-sectional area of the second tube to the interior diameter and cross-sectional area of the first tube of the ETU. In addition, the results show that the tip of the jet tube (ETU) should be shaped differently from that of a conventional ET so that the distal tip of ETU is right on the anterior wall of the ETU and the beveled distal tip of the ETU should be facing down rather than facing left as in regular ET.

3. The advantage of using a fiber-optic catheter rather than a $PetCO_2$ monitoring catheter is the ability to directly view the vocal cord and to thus reducing incidence of injury. However, the efficiency of placing an ETU quickly by using a fiber-optic catheter is significantly lower than when a $PetCO_2$ monitoring catheter is used. Therefore, in apnea patients who need emergent intubation, a $PetCO_2$ monitoring catheter is recommended to facilitate the intubation, although the fiber-optic guide can be used if the patient keeps breathing spontaneously.

C. Complications: The possible complications of using the ETU are gastric distension, throat swelling and barotraumas. An oral gastric tube before intubation can prevent the gastric distension. Minimizing the times of repeated intubation decrease the chances of throat swelling. As long as the airway is maintained unobstructed and no obstruction of expiration occurs during the intubation, it is believed that barotraumas can be mostly prevented.

Various other modifications can be made in the details of the various embodiments of the apparatus and methods of the present invention, all within the scope and spirit of the invention and defined by the appended claims.

What is claimed is:

1. An endotracheal device comprising an endotracheal unit comprising:
   a first tube having a proximate end, a distal end, an anterior surface, and a posterior surface, a first tube wall enclosing a first lumen having a cross-sectional area and having an exterior surface an interior surface (interior diameter<8 mm);

a second tube having proximate end, a distal end, and a second tube wall enclosing a second lumen having a cross-sectional area and an interior diameter of 1.6 mm to 2.3 mm, the second tube wall extending from the first tube wall, the cross-sectional area of the second lumen being smaller than the cross-sectional area of the first lumen, the distal end of the second tube extending beyond the distal end of the first tube;

a jet ventilator, which is connected to the second tube of the endotracheal unit with settings equivalent to a normal respiration rates; and a jet ventilation tube having an interior diameter ranging from 1.6 mm to 2.3 mm.

2. The endotracheal device according to claim 1, wherein the second tube wall extends from an anterior exterior surface of the first tube wall.

3. The endotracheal device according to claim 1, the endotracheal unit further comprising an insufflation cuff positioned proximate to the distal end of the first tube, and a third tube for inflating the insufflation cuff.

4. The endotracheal device according to claim 1, further comprising at least one patient monitoring device, the at least one patient monitoring device being selected from the class consisting of (1) one or more catheters for monitoring end-tidal $CO_2$, and (2) one or more visual monitoring devices for observing the vocal cord, the at least one monitoring device being positioned in the lumen of the first tube of the endotracheal unit.

5. The endotracheal device according to claim 1, further comprising a bendable, shape-retaining stylet for shaping the endotracheal unit.

6. The endotracheal device according to claim 1, further comprising a source of jet ventilation for providing jet ventilation through the second tube.

7. A method of intubation of a patient using an endotracheal device of claim 4, the method comprising:
a) positioning the distal end of the second tube under an epiglottis of the patient while aligning the first tube with the midline of; the patient's body;
b) starting jet ventilation via the second tube using the jet ventilator;
c) adjusting direction of the distal end of the second tube as indicated by the monitoring device;
d) advancing the monitoring device into the patient's trachea past the patient's vocal cord opening while continuing jet ventilation; and
e) sliding the endotracheal unit over the monitoring device into the trachea.

8. The method of intubation according to claim 7, wherein the at least one monitoring device comprises an end-tidal $CO_2$ monitoring catheter, and the method further comprises adjusting direction of the distal end of the second tube to obtain the maximum end-tidal $CO_2$ with a capnogram having a stable plateau.

9. The method of intubation according to claim 7, further comprising observing the patient's vocal cord(s) by at least one visual monitoring device.

10. The method of intubation according to claim 9, wherein the visual monitoring is by a fiber-optic scope.

11. The method of intubation according to claim 7, further comprising monitoring the chest rise and breath sound of the patient on the patient's exterior chest wall.

12. The method of intubation according to claim 7, further comprising shaping the endotracheal unit with a bendable, shape-retaining stylet.

13. The method of intubation according to claim 7, further comprising withdrawing the monitoring device from the jet endotracheal unit.

14. The method of intubation according to claim 7, further comprising discontinuing jet ventilation through the second tube, and providing ventilation to the patient through the first tube.

15. The method of intubation according to claim 14, further comprising capping the proximate end of the second tube.

16. The method of intubation according to claim 14, further comprising providing conventional ventilation to the patient through the first tube.

17. The method of intubation according to claim 14, further comprising providing jet ventilation to the patient through the first tube.

18. The method of intubation according to claim 7, wherein the endotracheal unit further comprises an inflatable insufflation cuff, and the method further comprises inflating the insufflation cuff after the endotracheal unit has been slid into the trachea of the patient.

19. The method of intubation according to claim 7, further comprising delivering medication to the patient through the second tube of the endotracheal unit.

20. The method of intubation according to claim 7, further comprising apply applying suction to the patient through the second tube of the endotracheal unit.

* * * * *